United States Patent [19]
Janssens et al.

[11] Patent Number: 5,629,308
[45] Date of Patent: May 13, 1997

[54] IMIDAZO [1,2-A] (PYRROLO, THIENO OR FURANO) [2,3-D] AZEPINE DERIVATIVES

[75] Inventors: Frans E. Janssens, Bonheiden; Gaston S. M. Diels, Ravels; Joseph E. Leenaerts, Rijkevorsel, all of Belgium

[73] Assignee: Janssen Pharmaceutica N.V., Beerse, Belgium

[21] Appl. No.: 433,386

[22] PCT Filed: Nov. 25, 1993

[86] PCT No.: PCT/EP93/03321

§ 371 Date: May 8, 1995

§ 102(e) Date: May 8, 1995

[87] PCT Pub. No.: WO94/13680

PCT Pub. Date: Jun. 23, 1994

[30] Foreign Application Priority Data

Dec. 4, 1992 [EP] European Pat. Off. ............ 92203778

[51] Int. Cl.$^6$ .................. A61K 31/55; C07D 487/14; C07D 491/147; C07D 495/14
[52] U.S. Cl. ............................................. 514/214; 540/578
[58] Field of Search ............................ 514/214, 215; 540/578

[56] References Cited

U.S. PATENT DOCUMENTS 5,461,050 10/1995 Janssens et al. .................... 514/214

FOREIGN PATENT DOCUMENTS 0518434 12/1992 European Pat. Off. .
WO92/06981 4/1992 WIPO .

OTHER PUBLICATIONS

Thornber et al., Isoterism and Molecular Modification in Drug Design, Chemical Society Reviews, vol. 8, pp. 563–580. 1979.

*Primary Examiner*—Johann Richter
*Assistant Examiner*—Richard S. Myers, Jr.
*Attorney, Agent, or Firm*—Charles J. Metz

[57] ABSTRACT

Antiallergic imidazo[1,2-a](pyrrolo, thieno or furano)[2,3-d]azepines of formula

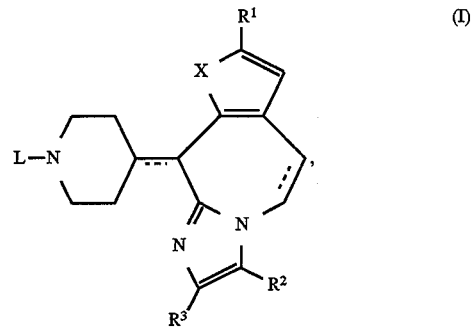

the pharmaceutically acceptable addition salts and stereochemically isomeric forms thereof, wherein each of the dotted lines independently represents an optional bond;

$R^1$ represents hydrogen, $C_{1-4}$alkyl, halo, ethenyl substituted with hydroxycarbonyl or $C_{1-4}$alkyloxycarbonyl, hydroxy$C_{1-4}$alkyl, formyl, hydroxycarbonyl or hydroxycarbonyl$C_{1-4}$alkyl;

$R^2$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl or hydroxycarbonyl;

$R^3$ represents hydrogen, $C_{1-4}$alkyl, hydroxy$C_{1-4}$alkyl, phenyl or halo;

X represents O, S or $NR_4$;

L represents hydrogen; $C_{1-6}$alkyl; substituted $C_{1-6}$alkyl; $C_{3-6}$alkenyl; $C_{3-6}$alkenyl substituted with aryl; or a radical of formula-Alk-Y-Het$^1$ (a-1), —Alk-NH-CO-Het$^2$ (a-2) or -Alk-Het$^3$ (a-3). Compositions comprising said compounds, processes of preparing the same and intermediates in the preparation thereof.

14 Claims, No Drawings

IMIDAZO [1,2-A] (PYRROLO, THIENO OR FURANO) [2,3-D] AZEPINE DERIVATIVES

CROSS-REFERENCE TO RELATED APPLICATIONS

This application is based upon PCT application Ser. No. PCT/EP 93/03321, filed Nov. 25, 1993, which claims priority from European Application Serial No. 92.203.778.3, filed on Dec. 4, 1992.

The present invention is concerned with novel imidazo [1,2-a](pyrrolo, thieno or furano)[2,3-d]azepine derivatives having antiallergic activity.

In EP-A-0,339,978 there are described (benzo- or pyrido) cyclohepta heterocyclics which are useful as PAF antagonists, antihistaminics and/or anti-inflammatory agents. In the J. Med. Chem., 26 (1983), 974–980 there are described some 1-methyl-4-piperidinylidene-9-substituted pyrrolo[2,1-b][3]benzazepine derivatives having neuroleptic properties.

In WO 92/06981 there are described substituted imidazobenzazepines and imidazopyridoazepines having and allergic and and-inflammatory activity. The compounds of the present invention differ structurally from the cited art-known compounds by the fact that the central 7-membered ring invariably contains a nitrogen atom of a fused imidazole ring, and by their favorable andallergic activity.

The present invention is concerned with novel imidazo [1,2-a](pyrrolo, thieno or furano)[2,3-d]azepines of formula

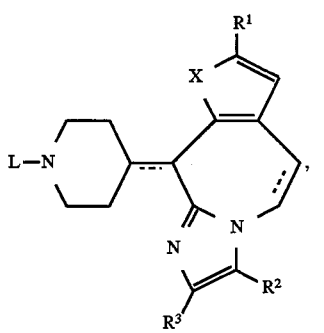

(I)

the pharmaceutically acceptable addition salts and stereochemically isomeric forms thereof, wherein each of the dotted lines independently represents an optional bond;

$R^1$ represents hydrogen, $C_{1-4}$alkyl, halo, ethenyl substituted with hydroxycarbonyl or $C_{1-4}$alkyloxycarbonyl, hydroxy$C_{1-4}$alkyl, formyl, hydroxycarbonyl or hydroxycarbonyl$C_{1-4}$alkyl;

$R^2$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl or hydroxycarbonyl;

$R^3$ represents hydrogen, $C_{1-4}$alkyl, hydroxy$C_{1-4}$alkyl, phenyl or halo;

X represents O, S or $NR_4$;

$R^4$ represents hydrogen, $C_{1-6}$alkyl or $C_{1-4}$alkylcarbonyl;

L represents hydrogen; $C_{1-6}$alkyl; $C_{1-6}$alkyl substituted with one substituent selected from the group consisting of hydroxy, $C_{1-4}$alkyloxy, hydroxycarbonyl, $C_{1-4}$alkyloxycarbonyl, $C_{1-4}$alkylaminocarbonyl, $C_{1-4}$alkyloxycarbonylamino, $C_{1-4}$alkyloxycarbonyl$C_{1-4}$alkyloxy, hydroxycarbonyl$C_{1-4}$alkyloxy, $C_{1-4}$alkylaminocarbonylamino, $C_{1-4}$alkylaminothiocarbonylamino, aryl and aryloxy; $C_{1-6}$alkyl substituted with both hydroxy and aryloxy; $C_{3-6}$alkenyl; $C_{3-6}$alkenyl substituted with aryl;

wherein each aryl is phenyl or phenyl substituted with halo, cyano, hydroxy, $C_{1-4}$alkyl, $C_{1-4}$alkyloxy or aminocarbonyl; or, L represents a radical of formula
—Alk-Y-Het$^1$(a-1),
—Alk-NH-CO-Het$^2$(a-2) or
—Alk-Het$^3$(a-3); wherein Alk represents $C_{1-4}$alkanediyl;

Y represents O, S or NH;

Het$^1$, Het$^2$ and Het$^3$ each represent furanyl, thienyl, oxazolyl, thiazolyl or imidazolyl each optionally substituted with one or two $C_{1-4}$alkyl substituents; pyrrolyl or pyrazolyl optionally substituted with formyl, hydroxy$C_{1-4}$alkyl, hydroxycarbonyl, $C_{1-4}$alkyloxycarbonyl or with one or two $C_{1-4}$alkyl substituents; thiadiazolyl or oxadiazolyl optionally substituted with amino or $C_{1-4}$alkyl; pyridinyl, pyrimidinyl, pyrazinyl or pyridazinyl each optionally substituted with $C_{1-4}$alkyl, $C_{1-4}$alkyloxy, amino, hydroxy or halo; and Het$^3$ may also represent 4,5-dihydro-5-oxo-1H-tetrazolyl substituted with $C_{1-4}$alkyl, 2-oxo-3-oxazolidinyl, 2,3-dihydro-2-oxo-1H-benzimidazol-1-yl or a radical of formula

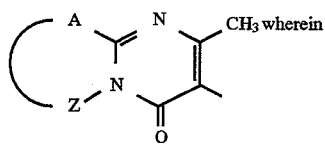

A-Z represents S-CH=CH, S-CH$_2$-CH$_2$, S-CH$_2$-CH$_2$-CH$_2$, CH=CH-CH=CH or CH$_2$-CH$_2$-CH$_2$-CH$_2$.

As used in the foregoing definitions halo defines fluoro, chloro, bromo and iodo; $C_{1-4}$alkyl defines straight and branched chain saturated hydrocarbon radicals having from 1 to 4 carbon atoms such as, for example, methyl, ethyl, propyl, 1-methylethyl, butyl, 1-methylpropyl, 2-methylpropyl and 1,1-dimethylethyl; $C_{1-6}$alkyl defines $C_{1-4}$alkyl radicals as defined hereinbefore and the higher homologs thereof having from 5 to 6 carbon atoms such as, for example, pentyl and hexyl; $C_{3-6}$alkenyl defines straight and branched chain hydrocarbon radicals containing one double bond and having from 3 to 6 carbon atoms such as, for example, 2-propenyl, 2-butenyl, 3-butenyl, 2-methyl-2-propenyl, 2-pentenyl, 3-pentenyl, 3,3-dimethyl-2-propenyl, hexenyl and the like; $C_{1-4}$alkanediyl defines bivalent straight or branched chain hydrocarbon radicals containing from 1 to 4 carbon atoms such as, for example, methylene, 1,1-ethanediyl, 1,2-ethanediyl, 1,3-propanediyl, 1,4-butanediyl and the like.

The term pharmaceutically acceptable addition salt as used hereinbefore defines the non-toxic, therapeutically active addition salt forms which the compounds of formula (I) may form. The compounds of formula (I) having basic properties may be converted into the corresponding therapeutically active, non-toxic acid addition salt forms by treating the free base form with a suitable amount of an appropriate acid following conventional procedures. Examples of appropriate acids are for example, inorganic acids, for example, hydrohalic acid, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetdcarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The compounds of formula (I) having acidic properties may be convened in a similar manner into the corresponding therapeutically active, non-toxic base addition salt forms. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine. The term pharmaceutically acceptable addition salts also comprises the solvates which the compounds of formula (I) may form, e.g. the hydrates, alcoholates and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

Some compounds of the present invention may exist in different tautomeric forms and all such tautomeric forms are intended to be included within the scope of the present invention.

A particular group of compounds are those compounds of formula (I) wherein L is hydrogen; $C_{1-6}$alkyl; $C_{1-6}$alkyl substituted with one substituent selected from the group consisting of hydroxy, $C_{1-4}$alkyloxy, hydroxycarbonyl, $C_{1-4}$alkyloxycarbonyl, $C_{1-4}$alkyloxycarbonyl$C_{1-4}$alkyloxy, hydroxycarbonyl$C_{1-4}$alkyloxy, $C_{1-4}$alkylaminocarbonylamino, $C_{1-4}$alkylaminothiocarbonylamino, aryl and aryloxy; $C_{1-6}$alkyl substituted with both hydroxy and aryloxy; $C_{3-6}$alkenyl; $C_{3-6}$alkenyl substituted with aryl; or L represents a radical of formula Alk-Y-Het$^1$ (a-1), Alk-NH-CO-Het$^2$ (a-2) or Alk-Het$^3$ (a-3).

Interesting compounds of formula (I) are those compounds wherein $R^1$, $R^2$ and $R^3$ represent hydrogen.

Another group of interesting compounds of formula (I) are those wherein X represents S.

Yet another group of interesting compounds of formula (I) are those of formula

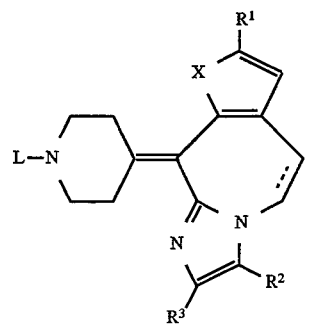

wherein the dotted line, X, L, $R^1$, $R^2$ and $R^3$ are as defined under formula (I).

Preferred compounds are those compounds of formula (I) wherein L is $C_{1-4}$alkyl.

The most preferred compound is: 6,10-dihydro-10-(1-methyl-4-piperidinylidene)-5H-imidazo[1,2-a]thieno[2,3-d]azepine the stereoisomers and the pharmaceutically acceptable addition salts thereof.

In the following paragraphs there are described different ways of preparing the compounds of formula (I). In order to simplify the structural formulae of the compounds of formula (I) and the intermediates intervening in their preparation, the imidazo[1,2-a](pyrrolo, thieno or furano)[2,3-d]azepine moiety will be represented by the symbol T hereinafter.

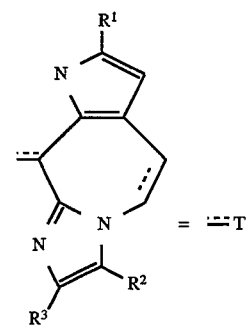

The compounds of formula (I) can be prepared by cyclizing an alcohol of formula (II) or a ketone of formula (III).

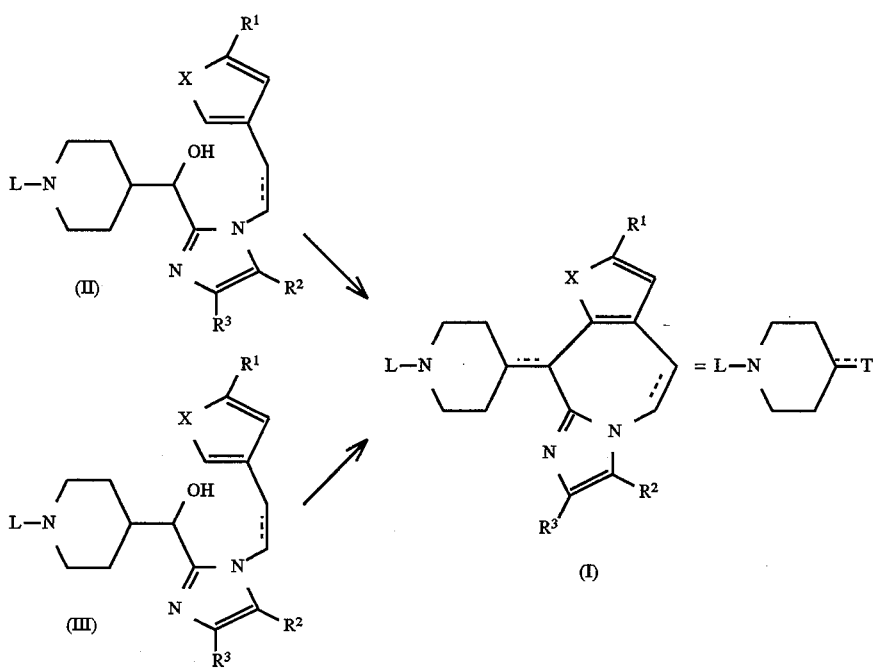

(II)

(III)

(I)

Said cyclization reaction is conveniently conducted by treating the intermediate of formula (II) or (III) with an appropriate acid, thus yielding a reactive intermediate which cyclizes to a compound of formula (I). Appropriate acids are, for example, strong acids, in particular superacid systems, e.g. methanesulfonic acid, trifluoromethanesulfonic acid, trifluoroacetic acid, methanesulfonic acid/ boron trifluoride, hydrofluoric acid/boron trifluoride, or Lewis acids, e.g. aluminum chloride, trimethylsilyl iodide, phosphorylchloride and the like. Obviously, only those compounds of formula (I) wherein L is stable under the given reaction conditions can be prepared according to the above reaction procedure.

In the foregoing and following preparations, the reaction mixture is worked up following art-known methods and the reaction product is isolated and, if necessary, further purified.

The compounds of formula (I) wherein the central ring of the tricyclic moiety does not contain an optional bond may also be prepared by cyclizing an intermediate of formula (IV).

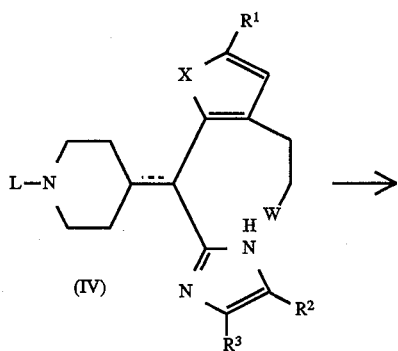

(IV)

-continued

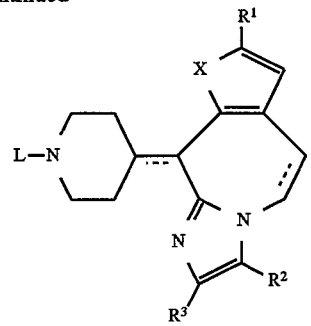

In formula (IV) and hereinafter W represents an appropriate leaving group such as, for example, halo, e.g. chloro, bromo and the like; or a sulfonyloxy group such as, for example, methanesulfonyloxy, 4-methylbenzenesulfonyloxy and the like. Said cyclization reaction can conveniently be conducted in a reaction-inert solvent such as, for example, an aromatic hydrocarbon, an alkanol, a ketone, an ether, a dipolar aprotic solvent, or a mixture of such solvents. The addition of an appropriate base such as, for example, an alkali or an earth alkaline metal carbonate, hydrogen carbonate, alkoxide, hydride, amide, hydroxide or oxide; or an organic base may be utilized to pick up the acid which is liberated during the course of the reaction. In some instances the addition of an iodide salt, preferably an alkali metal iodide, is appropriate. Somewhat elevated temperatures and stirring may enhance the rate of the reaction.

Alternatively, the compounds of formula (I) wherein a double bond exists between the piperidinyl and the imidazo [1,2-a](pyrrolo, thieno or furano)[2,3-d]azepine moiety, said compounds being represented by formula (I-a), can be prepared by dehydrating an alcohol of formula (V) or (VI).

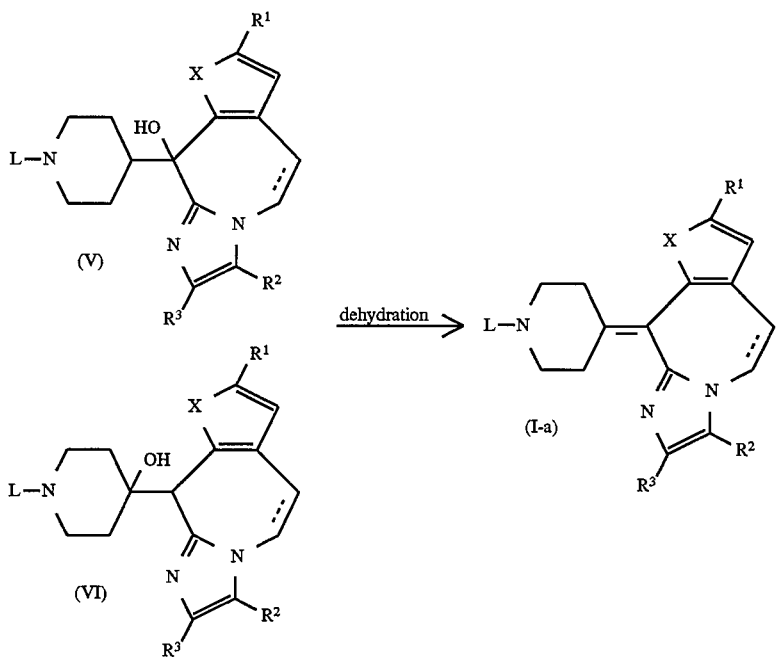

Said dehydration reaction can conveniently be conducted employing conventional dehydrating reagents following art-known methodologies. Appropriate dehydrating reagents are, for example, acids, e.g. sulfuric acid, phosphoric acid, phosphorous acid, hydrochloric acid, methanesulfonic acid, carboxylic acids, e.g. acetic acid, trifluoroacetic acid and mixtures thereof; anhydrides, e.g. acetic anhydride, phosphorus pentoxide and the like; other suitable reagents, e.g. zinc chloride, thionyl chloride, boron trifluoride etherate, phosphoryl chloride pyridine, potassium bisulfate, potassium hydroxide or phosphoryl chloride. Optionally, said dehydration reaction is conducted in a reaction-inert solvent such as, for example, a halogenated hydrocarbon, e.g. dichloromethane. In some instances said dehydration reaction may require heating the reaction mixture, more particularly up to the reflux temperature. Again, only those compounds of formula (I-a) wherein L is stable under the given reaction conditions can be prepared according to the above reaction procedure.

The compounds of formula (I) wherein L is $C_{1-6}$alkyl, said compounds being represented by the formula (I-b), can be convened into the compounds of formula (I) wherein L is hydrogen, said compounds being represented by the formula (I-c), in a number of manners. A first method involves dealkylating—carbonylating the compounds of formula (I-b) with a $C_{1-4}$alkylchloroformate and subsequently hydrolyzing the thus obtained compound of formula (VII-a).

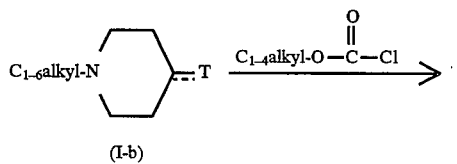

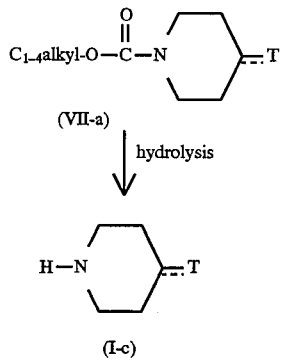

The reaction with the $C_{1-4}$alkylchloroformate is conveniently conducted by stirring and heating the starting material (I-b) with the reagent in an appropriate solvent and in the presence of a suitable base. Appropriate solvents are, for example, aromatic hydrocarbons, e.g. methylbenzene, dimethylbenzene, chlorobenzene; ethers, e.g. 1,2-dimethoxyethane, and the like solvents. Suitable bases are, for example, alkali or earth alkaline metal carbonates, hydrogen carbonates, hydroxides, or organic bases such as, N,N-diethylethanamine, N-(1-methylethyl)-2-propanamine, and the like. The compounds of formula (VII-a) are hydrolyzed in acidic or basic media following conventional methods. For example, concentrated acids such as hydrobromic, hydrochloric acid or sulfuric acid can be used, or alternatively bases such as alkali metal or earth alkaline metal hydroxides, e.g. sodium hydroxide or potassium hydroxide, in water, an alkanol or a mixture of water-alkanol may be used. Suitable alkanols are methanol, ethanol, 2-propanol and the like. In order to enhance the rate of the reaction it is advantageous to heat the reaction mixture, in particular up to the reflux temperature.

The compounds of formula (I-b) may also be converted directly into the compounds of formula (I-c) by stirring and heating them with an a-halo$C_{1-4}$alkyl chloroformate in an appropriate solvent such as, for example, a halogenated hydrocarbon, e.g. dichloromethane, trichloromethane; an aromatic hydrocarbon, e.g. methylbenzene, dimethylbenzene; an ether, e.g. 1,2-dimethoxyethane; an alcohol, e.g. methanol, ethanol, 2-propanol, optionally in the presence of a base such as, for example, an alkali or earth alkaline metal carbonate, hydrogen carbonate, hydroxide or an amine, e.g. N,N-diethylethanamine, N-(1-methylethyl)-2-propanamine, and the like.

The compounds of formula (I-c) can also be prepared by debenzylating a compound of formula (I-d) by catalytic hydrogenation in the presence of hydrogen and an appropriate catalyst in a reaction-inert solvent.

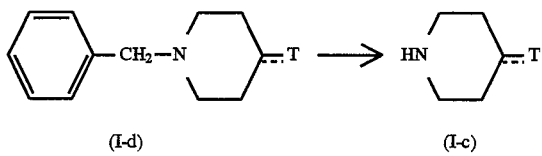

(I-d)                    (I-c)

A suitable catalyst in the above reaction is, for example, platinum-on-charcoal, palladium-on-charcoal, and the like. An appropriate reaction-inert solvent for said debenzylation reaction is, for example, an alcohol, e.g. methanol, ethanol, 2-propanol, and the like, an ester, e.g. ethyl acetate and the like, an acid, e.g. acetic acid and the like.

The compounds of formula (I) wherein L is other than hydrogen, said compounds being represented by formula (I-e) and said L by $L^1$, can be prepared by N-alkylating the compounds of formula (I-c) with a reagent of formula $L^1$-W (VIII).

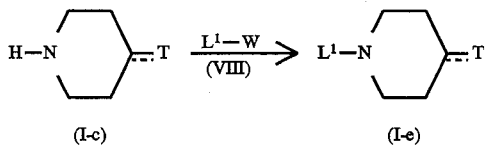

(I-c)                    (I-e)

Said N-alkylation reaction can conveniently be conducted in a reaction-inert solvent such as, for example, an aromatic hydrocarbon, an alkanol, a ketone, an ether, a dipolar aprotic solvent, a halogenated hydrocarbon, or a mixture of such solvents. The addition of an appropriate base such as, for example, an alkali or an earth alkaline metal carbonate, hydrogen carbonate, alkoxide, hydride, amide, hydroxide or oxide, or an organic base may be utilized to pick up the acid which is liberated during the course of the reaction. In some instances the addition of an iodide salt, preferably an alkali metal iodide, is appropriate. Somewhat elevated temperatures and stirring may enhance the rate of the reaction. Alternatively, said N-alkylation may be carried out by applying art-known conditions of phase transfer catalysis reactions.

The compounds of formula (I) wherein L is $C_{1-6}$alkyl or substituted $C_{1-6}$alkyl, can also be prepared by reductive N-alkylation of the compounds of formula (I-c) following art-known procedures. The compounds of formula (I) wherein L is $C_{1-6}$alkyl or substituted $C_{1-6}$alkyl can further be prepared by the addition reaction of the compounds of formula (I-c) with a suitable alkene following art-known procedures. The compounds of formula (I) wherein L is $C_{1-6}$alkyl substituted with hydroxy can be prepared by reacting a compound of formula (I-c) with a suitable epoxide following art-known procedures. The compounds of formula (I) with a double bond in the tricyclic moiety and/or a double bond bridging the tricyclic moiety and the piperdine may be reacted into compounds of formula (I) with a single bond at either one or both of the beforementioned sites following art-known reduction procedures.

The compounds of formula (I) may further be converted into each other following art-known functional group transformation procedures.

Some examples of such procedures are cited hereinafter. The compounds of formula (I) containing an amino substituent can be obtained by the hydrolysis of a corresponding amide compound. Amino groups may be N-alkylated or N-acylated following art-known procedures. Further, the compounds of formula (I) containing ester groups may be converted in the carboxylic acids by art-known hydrolysis procedures. Aromatic ethers may be converted in the corresponding alcohols following art-known ether cleavage procedures. Compounds of formula (I) containing a hydroxy substituent may be O-alkylated or O-acylated following art-known procedures.

The compounds of formula (VII-a) intervening in the preparations described hereinbefore are novel and have especially been developed for use as intermediates in said preparations. Consequently, the present invention also relates to novel compounds of formula

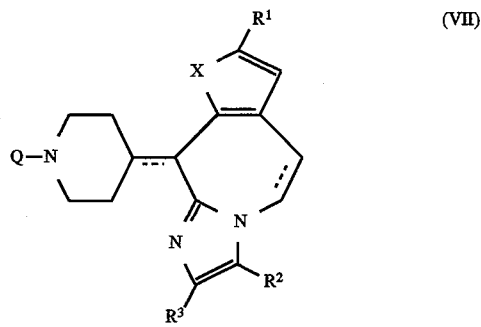

the addition salts and the stereochemically isomeric forms thereof, wherein X, $R^1$, $R^2$ and $R^3$ are as defined for the compounds of formula (I); and Q represents $C_{1-6}$alkyloxycarbonyl, $C_{1-4}$alkylcarbonyl or $C_{1-6}$alkyl substituted with halo, cyano, amino, or methylsulfonyloxy.

Particularly interesting compounds of formula (VII) are those wherein Q represents $C_{1-6}$alkyloxycarbonyl, the addition salts and the stereochemically isomeric forms thereof.

In the following paragraphs there are described several methods of preparing the starting materials employed in the foregoing preparations.

The intermediates of formula (II) can be prepared from the corresponding ketones of formula (III) by reduction.

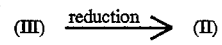

Said reduction can conveniently be conducted by reacting the starting ketone (III) with hydrogen in a solvent such as, for example, an alcohol, e.g. methanol, ethanol; an acid, e.g. acetic acid; an ester, e.g. ethyl acetate; in the presence of a hydrogenation catalyst, e.g. palladium-on-charcoal, platinum-on-charcoal, Raney Nickel. In order to enhance the rate of the reaction, the reaction mixture may be heated and, if desired, the pressure of the hydrogen gas may be raised. Alternatively, the alcohols of formula (II) can also be prepared by reducing the ketones (III) with a reducing agent such as, for example, lithium aluminum hydride, sodium borohydride, sodium cyanoborohydride and the like in a suitable solvent such as, for example, an ether, e.g. 1,1'-oxybisethane, tetrahydrofuran and the like; an alcohol, e.g. methanol, ethanol and the like.

The ketones of formula (III) can be prepared by the addition of a compound of formula (IX) to a reagent of formula (X) following art-known procedures.

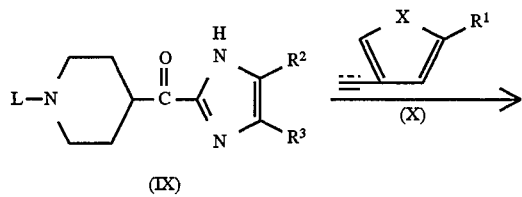

(IX)

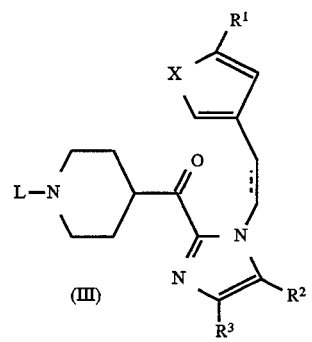

(III)

The ketones of formula (III) wherein the dotted line is not an optional bond can be prepared by N-alkylating an intermediate of formula (IX) with a reagent of formula (XI) wherein W represents a reactive leaving group as defined hereinbefore.

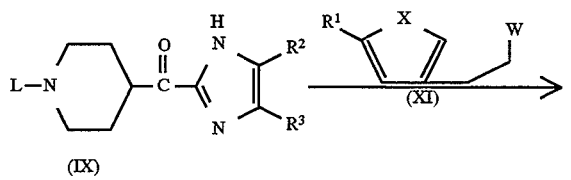

(IX)

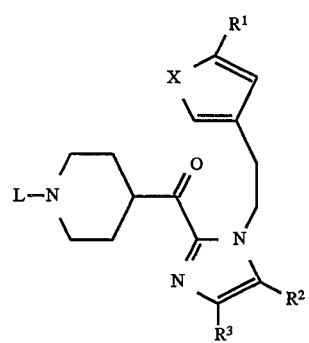

Said N-alkylation reaction can conveniently be conducted following the procedures employed in preparing the compounds of formula (I-e) from the compounds of formula (I-c).

The intermediates of formula (V) can be prepared by addition of a Grignard reagent (XII) to a ketone of formula (XIII) in a reaction-inert solvent, e.g. tetrahydrofuran.

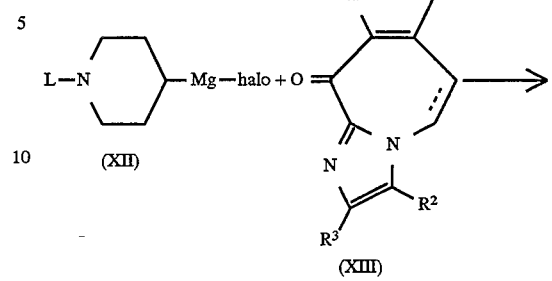

(XII)   (XIII)

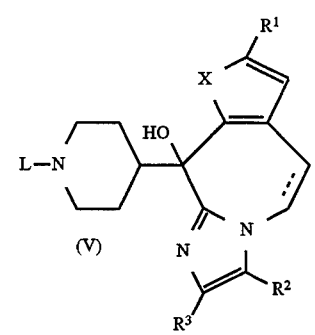

(V)

The tricyclic ketones of formula (XIII) in turn are prepared from intermediates of formula (XIV) by oxidation with a suitable oxidizing reagent in a reaction-inert solvent.

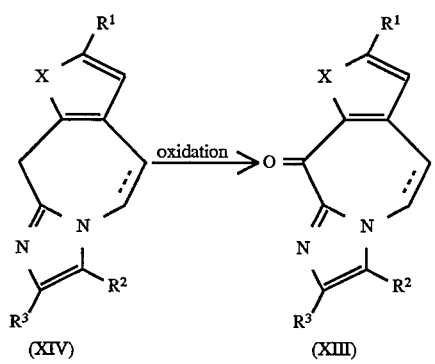

(XIV)   (XIII)

Suitable oxidizing reagents are, for example, manganese dioxide, selenium dioxide, ceric ammonium nitrate and the like. Reaction-inert solvents are, for example, halogenated hydrocarbons, e.g. dichloromethane, trichloromethane and the like.

The compounds of formula (XIV) wherein the dotted lines do not represent an optional bond can be prepared from the corresponding compounds of formula (XIV) wherein said dotted lines do represent an optional bond, following art-known hydrogenation procedures, e.g. by reaction with hydrogen in the presence of a hydrogenation catalyst.

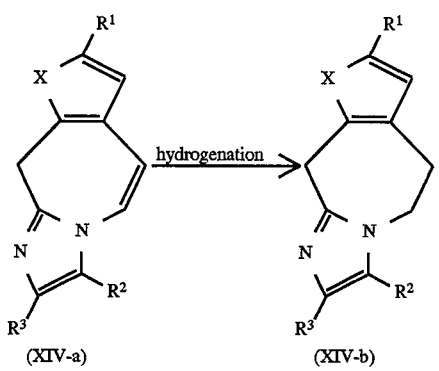

(XIV-a)  (XIV-b)

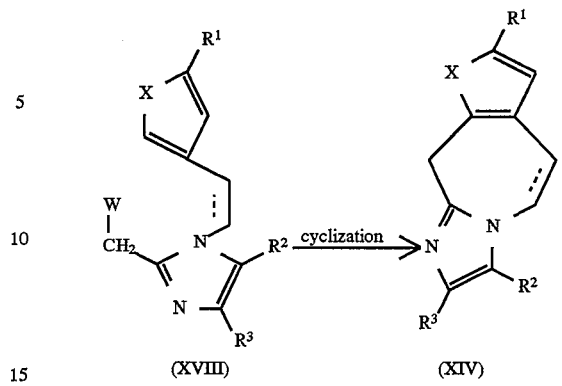

(XVIII)  (XIV)

The intermediates of formula (XIV-a) can be prepared from a benzazepine of formula (XV) by reaction with a reagent of formula (XVI) and cyclization of the thus obtained intermediate (XVII) in an acidic medium. In (XVI) R represents $C_{1-4}$alkyl or both radicals R taken together represent $C_{2-6}$alkanediyl, e.g. 1,2-ethanediyl, 1,3-propanediyl, 2,2-dimethyl- 1,3-propanediyl.

Said cyclization reaction is conveniently conducted in the presence of a Lewis acid, e.g. aluminum chloride, and the like. In some instances it may be appropriate to supplement the reaction mixture with a suitable amount of sodium chloride.

The intermediates of formula (V) can also be prepared from the cyclization of an intermediate of formula (III) in the presence of an acid in a reaction-inert solvent.

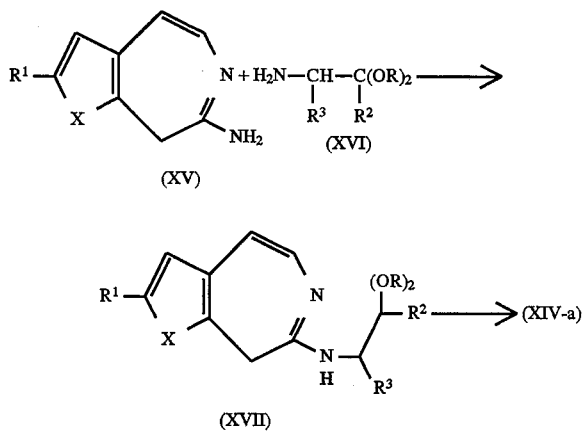

The preparation of (XVII) is conveniently conducted by stirring and heating the reactants in a reaction-inert solvent such as, for example, an alcohol, e.g. methanol, ethanol and the like. The cyclization reaction to the intermediates of formula (XIV-a) is conducted by stirring and heating the starting material (XVII) in a carboxylic acid such as, for example, acetic acid, propanoic acid, optionally in admixture with a mineral acid such as, for example, hydrochloric acid.

The intermediates of formula (XIV) can also be prepared from cyclization of an intermediate of formula (XVIII).

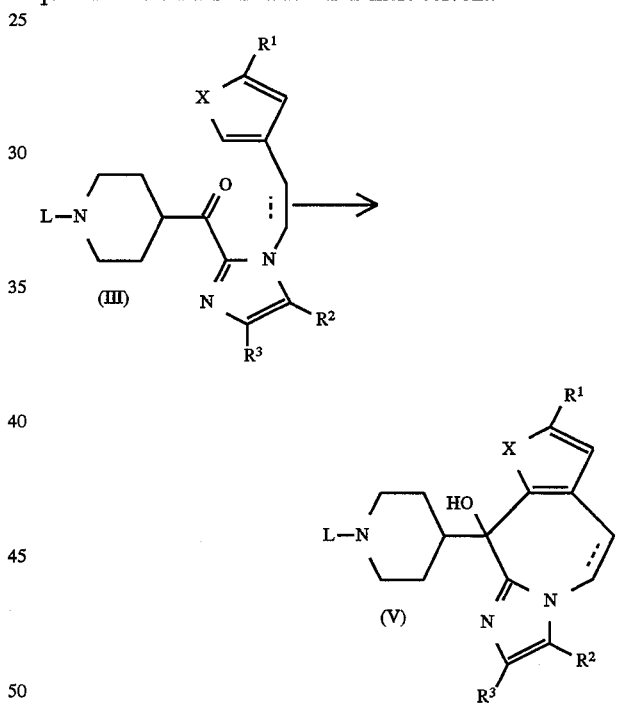

An appropriate acid in the above reaction is, for example, a Lewis acid, e.g. tin(IV)chloride and the like. A suitable reaction-inert solvent is, for example, a halogenated hydrocarbon, e.g. dichloromethane, 1,2-dichloroethane, and the like.

The intermediates of formula (VI) can be prepared by reaction of a ketone of formula (XIX) with an intermediate of formula (XIV) in the presence of e.g. lithium diisopropyl amide in a reaction-inert solvent, e.g. tetrahydrofuran.

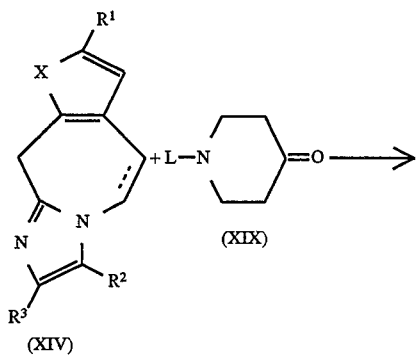

(XIX)

(XIV)

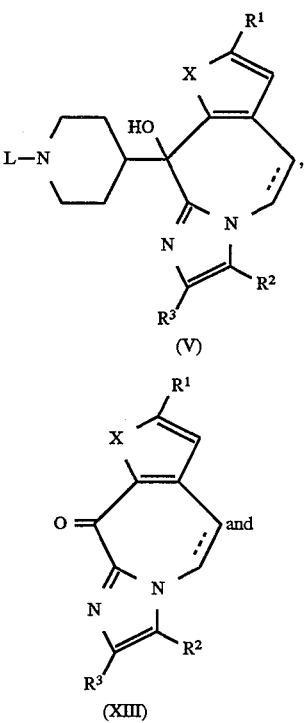

The compounds of formula (V) or (VI) wherein the dotted line represents a double bond may be converted into the compounds of formula (V) or (VI) wherein the dotted line is a single bond upon art-known reduction procedures.

The compounds of formula (V), (XIII) and (XIV) intervening in the preparations described hereinbefore are novel and have especially been developed for use as intermediates in said preparations. Consequently, the present invention also relates to novel compounds of formula

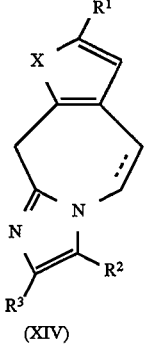

(XIV)

the addition salt forms thereof and the stereochemically isomeric forms thereof, wherein the dotted line, L, $R^1$, $R^2$, $R^3$ and X are as defined under formula (I).

The compounds of formula (I) and some of the compounds of formula (VII), in particular those wherein Q represents $C_{1-6}$alkyloxycarbonyl, the addition salts and the stereochemically isomeric forms thereof, possess useful pharmacological properties. In particular they are active antiallergic agents, which activity can clearly be demonstrated by the test results obtained in a number of indicative tests. Antihistaminic activity can be demonstrated in 'Protection of Rats from Compound 48/80—induced Lethality' test (Arch. Int. Pharmacodyn. Ther., 234, 164–176, 1978). The $ED_{50}$-values for the compounds 1, 3, 5, 6, 8–12, 14–19, 21–23, 27, 29–32 and 35–37 were found to be equal or below 0.31 mg/kg.

An advantageous feature of the compounds of the present invention resides in their excellent oral activity; the present compounds when administered orally have been found to be practically equipotent with the same being administered subcutaneously.

An interesting feature of the present compounds relates to their fast onset of action and the favorable duration of their action.

In view of their antiallergic properties, the compounds of formula (I) and the compounds of formula (VII) and their addition salts are very useful in the treatment of a broad range of allergic diseases such as, for example, allergic rhinitis, allergic conjunctivitis, chronic urticaria, allergic asthma and the like.

In view of their useful antiallergic properties the subject compounds may be formulated into various pharmaceutical forms for administration purposes. To prepare the antiallergic compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions: or solid carders such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on or as an ointment. Addition salts of the subject compounds due to their increased water solubility over the corresponding base form, are obviously more suitable in the preparation of aqueous compositions. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention also relates to a method of treating warm-blooded animals suffering from said allergic diseases by administering to said warm-blooded animals an effective antiallergic amount of a compound of formula (I) or a compound of formula (VII), or an addition salt form thereof. In general it is contemplated that an effective antiallergic amount would be from about 0.001 mg/kg to about 20 mg/kg body weight, and more preferably from about 0.01 mg/kg to about 5 mg/kg body weight.

The following examples are intended to illustrate and not to limit the scope of the present invention in all its aspects.

Experimental Part

A. Preparation of the Intermediate Compounds

EXAMPLE 1 a) A mixture of ethyl 2-thiopheneethanimidate monohydrochloride (ester) (0.05 mol) in tetrahydrofuran (100 ml) was stirred under nitrogen. 2,2-dimethoxyethanamine (0.05 mol) was added portionwise upon cooling and the mixture was stirred overnight. The mixture was evaporated, yielding 15.6 g (100%) of N-(2,2-dimethoxyethyl)-2-thiopheneethanimidamide monohydrochloride (interm. 1).

b) A mixture of intermediate (1) (0.05 mol) in acetic acid (50 ml) and a solution of hydrobromic acid in acetic acid 30% (50 ml) was stirred at 50° C. for 24 hours. The mixture was evaporated and the residue was taken up in water. The mixture was filtered over hyflo and alkalized with sodium hydroxide. The precipitate was filtered off, washed with water, taken up in tetrahydrofuran, decolorized with norrit and dried (MgSO$_4$). The mixture was filtered off, evaporated and the residue was stirred in hexane. The precipitate was filtered off and dried, yielding 4.4 g (53.6%) of 8H-thieno[2,3-d]azepin-7-amine (interm. 2).

c) A mixture of intermediate (2) (0.027 mol) and 2,2-dimethoxyethanamine (0.054 mol) in methanol (100 ml) was stirred and refluxed overnight. The mixture was evaporated, yielding 10 g (100%) of N-(2,2-dimethoxyethyl)-8H-thieno[2,3-d]azepino7-amine (interm. 3).

d) A mixture of intermediate (3) (0.027 mol) in acetic acid (95 ml) and hydrochloric acid (12.5 ml) was stirred at 70° C. overnight. The mixture was evaporated, the residue was taken up in water, alkalized with sodium hydroxide and extracted with dichloromethane. The organic layer was separated, dried and evaporated, yielding 3.4 g (67%) of 10H-imidazo[1,2-a]thieno[2,3-d]azepine (interm. 4).

e) A mixture of intermediate (4) (0.018 mol) and manganese dioxide (17 g) in dichloromethane (200 ml) was stirred at 40° C. for 5 days. Trichloromethane (200 ml) was added and the mixture was refluxed for 30 minutes. The mixture was filtered hot over hyflo, washed with dichloromethane and evaporated. The residue was boiled up in acetonitrile and cooled. The precipitate was filtered off and dried, yielding 1.53 g (42%) of 10H-imidazo[1,2-a]thieno[2,3-d]azepin-10-one (interm. 5).

f) Iodine (few crystals) was added upon stirring to a mixture of magnesium turnings (0.01 mol) in tetrahydrofuran (2 ml) under nitrogen. The mixture was heated till reflux, 4-chloro-1-methylpiperidine (0.01 mol) dissolved in tetrahydrofuran (5 ml) was added dropwise and the mixture was refluxed for 2 hours. Tetrahydrofuran (5 ml) was added. Intermediate (5) (0.0075 mol) was added portionwise (temp. 55°–60° C.) and the mixture was refluxed for 1 hour. The mixture was cooled, decomposed with a NH$_4$Cl-solution and extracted with dichloromethane/methanol. The organic layer was dried and evaporated. The residue was purified by column chromatography over silica gel (eluent: CH$_2$Cl$_2$/CH$_3$OH 95/5 CH$_2$Cl$_2$/(CH$_3$OH/NH$_3$) 95/5). The pure fractions were collected and evaporated, yielding 1.6 g (71%) (±)-10-(1-methyl-4-piperidinyl)-10H-imidazo[1,2-a]thieno[2,3-d]azepin-10-ol (interm. 6).

g) A mixture of intermediate (6) (0.01 mol) was hydrogenated in methanol (100 ml) overnight with palladium on activated carbon (10%) (2 g) as a catalyst. The catalyst was filtered off and hydrogenated further overnight. After uptake of hydrogen (1 eq.), the catalyst was filtered off. The residue was evaporated and purified by column chromatography over silica gel (eluent: CH$_2$Cl$_2$/(CH$_3$OH/NH$_3$) 95/5). The pure fractions were collected and evaporated, yielding 2.3 g of product. A sample (1.15 g) was crystallized from acetonitrile, yielding 0.5 g (16%) (±)-6,10-dihydro-10-(1-methyl-4-piperidinyl)-5H-imidazo[1,2-a]thieno[2,3-d]azepin-10-ol (interm. 7).

EXAMPLE 2 a) A dispersion of sodium hydride in mineral oil (50%) (0.088 mol) was added portionwise in N,N-dimethylformamide (150 ml) under nitrogen with stirring. (1H-imidazol-2-yl)-(1-methyl-4-piperidinyl)methanone (0.08 mol) was added portionwise and the mixture was stirred for 1 hour. 3-Thiopheneethanol methanesulfonate (ester) (0.086 mol) dissolved in a little N,N-dimethylformamide was added dropwise and the mixture was stirred on an oil bath at 60° C. overnight. The mixture was cooled, decomposed with water and extracted with dichloromethane. The organic layer was dried, filtered off and evaporated. The residue was purified by column chromatography over silica gel (eluent: CH$_2$Cl$_2$/(CH$_3$OH/NH$_3$) 95/5). The pure fractions were collected and evaporated, yielding 15 g (61.8%) of (1-methyl-4-piperidinyl)[1-[2-(3-thienyl)ethyl]-1H-imidazol-2-yl]methanone (interm. 8).

b) A mixture of intermediate (8) (0.02 mol) in 1,2-dichloroethane (100 ml) was stirred under nitrogen. Tin(IV) chloride (0.08 mol) was added dropwise at room temperature and the mixture was stirred at 80° C. for 2 hours. The mixture was cooled, poured into ice, alkalized with potassium carbonate, extracted with dichloromethane and ethanol and evaporated. The residue was purified by column chromatography over silica gel (eluent $CH_2Cl_2/(CH_3OH/NH_3)$ 95/5). The pure fractions were collected and evaporated. The residue was crystallized from acetonitrile. The precipitate was filtered off and dried, yielding 2.2 g (36.7%) of (±)-6,10-dihydro-10-(1-methyl-4-piperidinyl)-5H-imidazo[1,2-a]thieno[2,3-d]azepin-10-ol; mp. 176.6° C. (interm. 7).

B. Preparation of the Final Compounds

EXAMPLE 3 a) A mixture of intermediate (6) (0.005 mol) in phosphorus oxychloride (50 ml) was stirred and refluxed for 2 hours. The mixture was evaporated and the residue was taken up in water, alkalized with sodium hydroxide and extracted with dichloromethane/methanol. The organic layer was separated, dried and evaporated. The residue was purified on a glass filter over silica gel (eluent: $CH_2Cl_2/CH_3OH$ 95/5/ $CH_2Cl_2/(CH_3OH/NH_3)$ 95/5). The pure fractions were collected and evaporated. The residue (1.2 g) was crystallized from acetonitrile, yielding 0.3 g (21%) of 10-(1-methyl-4-piperidinylidene)-10H-imidazo-[1,2-a]thieno[2,3-d]azepine; mp. 152.2° C. (comp. 1).

EXAMPLE 4

Intermediate (7) (0.237 mol) and phosphoric acid 98% (1200 g) were stirred under nitrogen at 80° C. for 4 hours. The mixture was poured into ice, alkalized with sodium hydroxide and extracted with dichloromethane. The organic layer was dried ($MgSO_4$), filtered off and evaporated. The residue was purified by column chromatography over silica gel (eluent: $CH_2Cl_2/(CH_3OH/NH_3)$ 95/5). The pure fractions were collected and evaporated, yielding 3.5 g (5.2%) of (±)-10-(1-methyl-4-piperidinyl)-10H-imidazo[1,2-a]thieno[2, 3-d]azepine (comp. 2).

In a similar way there was prepared:
6,10-dihydro-10-(1-methyl-4-piperidinylidene)-5H-imidazo [1,2-a]thieno[2,3-d]azepine (E)-2-butenedioate (1:2) ethanolate (2:1); mp. 164.7° C. (comp. 3).

EXAMPLE 5 a) A mixture of compound (1) (0.0095 mol) and N,N-diethylethanamine (0.19 mol) in methylbenzene (1.51) was stirred and refluxed. Carbonochloridic acid ethyl ester (0.475 mol) was added dropwise and the mixture was refluxed for 2 hours. The mixture was cooled, water was added, alkalized with potassium carbonate and extracted with methylbenzene. The organic layer was separated, dried and evaporated. The residue was purified by column chromatography over silica gel (eluent: $CH_2Cl_2/CH_3OH$ 95/5). The pure fractions were collected and evaporated. The residue (24 g) was stirred in 2,2'-oxybispropane and filtered off. The precipitate was recrystallized from acetonitrile, yielding 17.3 g (53.3%) of ethyl 4-(10H-imidazo[1,2-a]thieno[2,3-d]azepin-10-ylidene)-1-piperidinecarboxylate; mp. 176.5° C. (comp. 4).

In a similar way there was prepared:
ethyl 4-(5,6-dihydro-10H-imidazo[1,2-a]thieno[2,3-d]azepin-10-ylidene)-1-piperidine-carboxylate; mp. 181.5° C. (comp. 5).

b) A mixture of compound (4) (0.05 mol) and potassium hydroxyde (0.5 mol) in 2-propanol (250 ml) was stirred and refluxed for 8 hours. The residue was evaporated, taken up in water and extracted with dichloromethane. The organic layer was separated, dried and evaporated. The residue was purified on a glass filter over silica gel (eluent: $CH_2Cl_2/ (CH_3OH/NH_3)$ 90/10). The pure fractions were collected and evaporated, yielding 13 g of product. A sample (3 g) was converted into the (E)-2-butenedioic acid salt (2:1) in ethanol, yielding 1.77 g of 10-(4-piperidinylidene)-10H-imidazo[1,2-a]-thieno-[2,3-d]azepine (E)-2-butenedioate (2:1); mp. 275.0° C. (comp. 6).

In a similar way there was prepared:
6,10-dihydro-10-(4-piperidinylidene)-5H-imidazo[1,2-a] thieno[2,3-d]azepine (E)-2-butenedioate mp. 252.7° C. (comp. 7).

EXAMPLE 6 a) A mixture of 1-(2-chloroethyl)-4-methoxybenzene (0.012 mol), compound (7) (0.01 mol) and N,N-diethylethanamine (0.05 mol) in N,N-dimethylacetamide (50 ml) was stirred at 80° C. on an oil bath for 16 hours and then at 90° C. for 24 hours. The mixture was cooled and evaporated. The residue was taken up in water, alkalized with potassium carbonate and extracted with dichloromethane. The organic layer was dried, filtered off and evaporated. The residue was purified by column chromatography over silica gel (eluent: $CH_2Cl_2/(CH_3OH/NH_3)$ 95/5). The suitable fractions were collected and evaporated. The residue (3 g) was purified again by HPLC (eluent: $CH_2Cl_2/CH_3OH$ 97/3). The pure fractions were collected and evaporated. The residue (1.1 g) was converted into the ethanedioic acid salt (1:2) in ethanol, yielding 0.8 g (11.4%) of product. The product was crystallized twice from methanol and dried in a pistol at 100° C., yielding 0.6 g (8.5%) of 6,10-dihydro-10-[1-[2-(4-methoxyphenyl)ethyl]-4-piperidinylidene]-5H-imidazo[1,2-a]thieno[2,3-d]azepine ethanedioate(1:2); mp. 172.5° C. (comp. 8).

In a similar way there were prepared:
1-ethyl-1,4-dihydro-4-[2-[4-(10H-imidazo[1,2-a]thieno[2, 3-d]azepin-10-ylidene)-1-piperidinyl]ethyl]-5H-tetrazol-5-one; mp. 181.2° C. (comp. 9);

3-[2[4-(10H-imidazo[1,2-a]thieno[2,3-d]azepin-10-ylidene) -1-piperidinyl]ethyl]-2-oxazolidinone; mp. 189.9° C. (comp. 10);

3-[2-[4-(10H-imidazo[1,2-a]thieno[2,3-d]azepin-10-ylidene)-1-piperidinyl]ethyl]-2-methyl-4H-pyrido[1,2-a] pyrimidin-4-one (E)-2-butenedioate(2:3); mp. 222.7° C. (comp. 11);

6-[2-[4-(5,6-dihydro-10H-imidazo[1,2a]thieno[2,3-d] azepin-10-ylidene)-1-piperidinyl]ethyl]-7-methyl-5H-thiazolo[3,2-a]pyrimidin-5-one (E)-2-butenedioate (2:7); mp. 213.1° C. (comp. 12);

1-[2-[4-(5,6-dihydro-10H-imidazo[1,2-a]thieno[2,3-d] azepin-10-ylidene)-1-piperidinyl]ethyl]-4-ethyl-1,4-dihydro-5H-tetrazol-5-one; mp. 163.3° C. (comp. 13);

1-[3-[4-(5,6-dihydro-10H-imidazo[1,2-a]thieno[2,3-d] azepin-10-ylidene)-1-piperidinyl]propyl]-1,3-dihydro-2H-benzimidazol-2-one cyclohexylsulfamate (1:2) ethanolate (2:1); mp. 174.7° C. (comp. 14);

3-[2-[4-(5,6-dihydro-10H-imidazo[1,2-a]thieno[2,3-d] azepin-10-ylidene)-1-piperidinyl]ethyl]-2-oxazolidinone ethanedioate(1:2). hemihydrate; mp. 171.6° C. (comp. 15);

10-[1-(2-ethoxyethyl)-4-piperdinylidene]-6,10-dihydro-5H-imidazo[1,2-a]thieno[2,3-d]azepine cyclohexylsulfamate (1:3) (comp. 16);

4-(5,6-dihydro-10H-imidazo[1,2-a]thieno[2,3-d]azepin-10-ylidene)-N-(1-methylethyl)-1-piperidinepropanamide; mp. 175.7° C. (comp. 17);

3-[2-[4-(5,6-dihydro-10H-imidazo[1,2-a]thieno[2,3-d]azepin-10-ylidene)-1-piperidinyl]ethyl]-2-methyl-4H-pyrido[1,2-a]pyrimidin-4-one; mp. 211.1° C. (comp. 18);

6-[2-[4-(5,6-dihydro-10H-imidaz[2-a]thieno[2,3-d]azepin-10-ylidene)-1-piperidinyl]ethyl]-2,3-dihydro-7-methyl-5H-thiazolo[3,2-a]pyrimidin-5-one (E)-2-butenedioate (2:3); mp. 209.1° C. (comp. 19);

ethyl [2-[4-(5,6-dihydro-10H-imidazo[1,2-a]thieno[2,3-d]azepin-10-ylidene)-1-piperidinyl]ethyl]carbamate (comp. 20);

10-[1-[3-(4-fluorophenoxy)propyl]-4-piperidinylidene]-6,10-dihydro-5H-imidazo-[1,2-a]thieno[2,3-d]azepine cyclohexylsulfamate(1:3) (comp. 21);

7-[2-[4-(5,6-dihydro-10H-imidazo[1,2-a]thieno[2,3-d]azepin-10-ylidene)-1-piperidin-yl]ethyl]3,4-dihydro-8-methyl-2H,6H-pyrimido[2,1-b][1,3]thiazin-6-one; mp. 221.8° C. (comp. 22);

(E)-6,10-dihydro-10-[1-(3-phenyl-2-propenyl)-4-piperidinylidene]-5H-imidazo[1,2-a]thieno[2,3-d] azepine. ethanedioate(1:2). hemihydrate; mp. 183.7° C. (comp. 23);

1-acetyl-4-(5,6-dihydro-10H-imidazo[1,2-a]thieno[2,3d] azepin-10-ylidene)piperidine hemihydrate (comp. 24); and ethyl [2-[4-(5,6-dihydro-10H-imidazo[1,2-a]thieno[2,3-d] azepin-10-ylidene)-1-piperidinyl]ethoxy]acetate (comp. 25).

b) A mixture of compound (8) (0.01 mol) and sodium sulfite (0.1 g) in a solution of hydrobromic acid in water 48% (100 ml) was stirred and refluxed for 4 hours. The solvent was evaporated. The residue was stirred in water and this mixture was alkalized with potassium carbonate. The mixture was extracted with dichloromethane. The separated organic layer was dried (MgSO$_4$), filtered and the solvent was evaporated. The residue was purified over silica gel on a glass filter (eluent: CH$_2$Cl$_2$/CH$_3$OH 95/5). The pure fractions were collected and the solvent was evaporated. The residue was crystallized from acetonitrile. The precipitate was filtered off and dried, yielding 0.53 g (14%) of 6,10-dihydro-10-[1-[2-(4-hydroxyphenyl)ethyl]-4-piperidinylidene]-5H-imidazo[1,2-a]thieno[2,3-d]azepine; mp.>200° C. (comp. 26).

EXAMPLE 7 a) A mixture of methyl 2-propenoate (0.024 mol) and compound (7) (0.02 mol) in methanol (100 ml) was stirred at room temperature for 6 hours. The mixture was evaporated and the residue was purified on a glass filter over silica gel (eluent: CH$_2$Cl$_2$/CH$_3$OH 95/5). The pure fractions were collected and evaporated. The residue was crystallized from 2,2'-oxybispropane/acetonitrile, yielding 4.5 g (63%) of methyl 4-(5,6-dihydro-10H-imidazo[1,2-a]thieno[2,3-d] azepin-10-ylidene)-1-piperidine-propanoate; mp. 108.5° C. (comp. 27).

In a similar way there was prepared:

6,10-dihydro-10-[1-[2-(2-pyridinyl)ethyl]-4-piperidinylidene]-5H-imidazo[1,2-a]thieno-[2,3-d] azepine; mp. 144.4° C. (comp. 28).

b) A mixture of compound (27) (0.0031 mol) in sodium hydroxide (0.01 mol), water (50 ml), ethanol (10 ml) and tetrahydrofuran (20 ml) was stirred at room temperature overnight. The mixture was evaporated till water and washed with dichloromethane. Hydrochloric acid 1N (10 ml) was added dropwise, the precipitate was filtered off and dried, yielding 0.51 g (48%) of 4-(5,6-dihydro-10H-imidazo[1,2-a]thieno[2,3-d]azepin-10-ylidene)-1-piperidinepropanoic acid hemihydrate; mp. 250.2° C. (comp. 29).

In a similar way there was prepared:

[2-[4-(5,6-dihydro-10H-imidazo[1,2-a]thieno[2,3-d]azepin-10-ylidene)-1-piperidinyl]-ethoxy]acetic acid; mp. 205.7° C. (comp. 30).

EXAMPLE 8 a) A mixture of compound (7) (0.017 mol) in methanol (200 ml) was stirred at room temperature. Oxirane (excess) was bubbled through for 3 hours and the mixture was stirred at room temperature for 1 hour. The mixture was evaporated and the residue was purified on a glass filter over silica gel (eluent: CH$_2$Cl$_2$/(CH$_3$OH/NH$_3$) 95/5 to 90/10). The pure fractions were collected and evaporated. The residue was crystallized from acetonitrile, yielding 4 g (75%) of 4-(5,6-dihydro-10H-imidazo[1,2-a]thieno[2,3-d]-azepin-10-ylidene)-1-piperidineethanol; mp. 154.8° C. (comp. 31).

b) A mixture of a dispersion of sodium hydride in mineral oil 50% (0.012 mol) in N,N-dimethylformamide (100 ml) was stirred under nitrogen at room temperature. A solution of compound (31) (0.008 mol) in N,N-dimethylformamide was added dropwise and the mixture was stirred at room temperature for 1 hour. 2-Chloropyrimidine (0.012 mol) was added portionwise and the mixture was stirred at room temperature for 1 hour. The mixture was warmed up till 50° C. and stirred at 50° C. for 48 hours. The mixture was cooled, decomposed with water and extracted with dichloromethane. The organic layer was dried (MgSO$_4$), filtered off and evaporated. The residue was purified on a glass filter over silica gel (eluent: CH$_2$Cl$_2$/CH$_3$OH 93/7). The pure fractions were collected and evaporated. The residue was converted into the cyclohexanesulfamic acid salt (1:3) in 2-propanone, yielding 1.27 g (17%) of 6,10-dihydro-10-[1-[2-(2-pyrimidinyloxy)ethyl]-4-piperidinylidene]5H-imidazo[1,2-a]thieno[2,3-d]azepine cyclohexylsulfamate (1:3); mp. 122.1° C. (comp. 32).

EXAMPLE 9

A mixture of compound (20) (0.01 mol) and potassium hydroxide (0.1 mol) in 2-propanol (50 ml) was stirred and refluxed for 3 hours. The mixture was evaporated, the residue was taken up in dichloromethane (300 ml), dried (MgSO$_4$), filtered over hyflo and evaporated. The residue was purified on a glass filter over silica gel (eluent: CH$_2$Cl$_2$/(CH$_3$OH/NH$_3$) 90/10). The pure fractions were collected and evaporated, yielding 2.8 g (89%) of 4-(5,6-dihydro-10H-imidazo[1,2-a]thieno[2,3-d]azepin-10-ylidene)-1-piperidineethanamine (comp. 33).

EXAMPLE 10

A mixture of ethyl (3,5-diethoxy-tetrahydro-2-furanyl) carboxylate (0.02 mol) and compound (33) (0.01 mol) in acetic acid (50 ml) was stirred at 80° C. on an oil bath for 2 hours. The mixture was evaporated. The residue was taken up in water, alkalized with potassium carbonate and extracted with dichloromethane. The organic layer was dried, filtered off and evaporated. The residue was purified by column chromatography over silica gel (eluent 1:CH$_2$Cl$_2$/CH$_3$OH 95/5 and eluent 2:CH$_2$Cl$_2$/(CH$_3$OH/NH$_3$) 95/5). The pure fractions were collected and evaporated. The residue was taken up in 2-propanone, decolourized with norit, filtered over hyflo and evaporated. The residue (3.7 g) was converted into the cyclohexanesulfamic acid salt (1:2)

in 2-propanol/2-propanone, yielding 2.36 g (28%) of ethyl 1-[2-[4-(5,6-dihydro-10H-imidazo[1,2-a]-thieno[2,3-d]azepin-10-ylidene)-1-piperidinyl]ethyl]-1H-pyrrole-2-carboxylate 2-propanolate (1:1). cyclohexylsulfamate (1:2); mp. 112.8° C. (comp. 34).

EXAMPLE 11

A mixture of 2-furancarboxylic acid (0.012 mol), 2-chloro1-methylpyridium iodide (0.012 mol) and N,N-diethylethanamine (0.024 mol) in dichloromethane (100 ml) was stirred for 1 hour. Compound (33) (0.01 mol) dissolved in dichloromethane was added dropwise and the mixture was stirred for 2 hours. Water was added, the mixture was stirred and separated. The aqueous layer was extracted with dichloromethane and purified by column chromatography over silica gel (eluent 1: $CH_2Cl_2/CH_3OH$ 95/5 and eluent 2: $CH_2Cl_2/(CH_3OH/NH3)$ 95/5). The pure fractions were collected and evaporated. The residue (4.4 g) was converted into the ethanedioic acid salt (1:2) in ethanol. The residue was recrystallized from methanol, yielding 2.6 g (43%) N-[2-[4-(5,6-dihydro-10H-imidazo[1,2-a]thieno [2, 3-d] azepin-10-ylidene)-1-piperidinyl]ethyl]-3-furancarboxamide ethanedioate(1:2). monohydrate; mp. 185.9° C. (comp. 35).

EXAMPLE 12

A mixture of 2-chloropyrimidine (0.012 mol), compound (33) (0.009 mol) and sodium hydrogen carbonate (0.015 mol) in ethanol (100 ml) was stirred and refluxed for 48 hours. The mixture was evaporated, the residue was taken up in water and extracted with dichloromethane. The residue was purified by column chromatography over silica gel (eluent 1: $CH_2Cl_2/CH_3OH$ 95/5 and eluent 2: $CH_2Cl_2/(CH_3OH/NH_3)$ 95/5). The pure fractions were collected and evaporated. The residue was crystallized from acetonitrile, yielding 1.72 g (48.9%) of product. The product was recrystallized from acetonitrile, yielding 0.64 g (16%) of N-[2-[4-(5,6-dihydro-10H-imidazo[1,2-a]thieno-[2,3-d]azepin-10-ylidene)-1-piperidinyl]ethyl]-2-pyrimidinamine; mp. 172.6° C. (comp. 36).

EXAMPLE 13

Methylisocyanate (0.012 mol) was added dropwise to a stirring mixture of compound (33) (0.01 mol) in tetrahydrofuran (100 ml) and the mixture was stirred overnight. The mixture was evaporated and the residue was purified by column chromatography over silica gel (eluent 1: $CH_2Cl_2/CH_3OH$ 95/5 and eluent 2: $CH_2Cl_2/(CH_3OH/NH_3)$ 95/5. The pure fractions were collected and evaporated. The residue was stirred up in 2,2'-oxybispropane. The precipitate was filtered off and dried. The residue was crystallized from 2-propanone, yielding 0.85 g (23%) of N-[2-[4-(5,6-dihydro-10H-imidazo[1,2-a]-thieno[2,3-d]azepin-10-ylidene)-1-piperidinyl]ethyl]-N'-methylurea; mp. 158.9° C. (comp. 37).

EXAMPLE 14

A mixture of compound (2) (0.012 mol) in acetic acid (6 ml) and ethanol (150 ml) was hydrogenated with palladium on activated carbon (7 g) as a catalyst at room temperature for 48 hours. After uptake of ethanol (1 eq.), the catalyst was filtered off and the filtrate was evaporated. The residue was taken up in water, alkalized with potassium carbonate and extracted with dichloromethane. The organic layer was dried, filtered off and evaporated. The residue was purified on a glass filter over silica gel (eluent: $CH_2Cl_2/(CH_3OH/NH_3)$ 95/5). The pure fractions were collected and evaporated. The residue was crystallized from 2,2'-oxybispropane, yielding 0.53 g (15%) of (±)-6,10-dihydro-10-(1-methyl-4-piperidinyl)-5H-imidazo[1,2-a]thieno[2,3-d]azepine; mp. 121.0° C. (comp. 38).

C. Composition Examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (D or a compound of formula (VII), a pharmaceutically acceptable acid addition salt or a stereochemically isomeric form thereof.

EXAMPLE 15: Oral drops 500 g of the A.I. is dissolved in 0.5 l of 2-hydroxypropanoic acid and 1.5 l of the polyethylene glycol at 60°–80° C. After cooling to 30°–40° C. there are added 35 l of polyethylene glycol and the mixture is stirred well. Then there is added a solution of 1750 g of sodium saccharin in 2.5 l of purified water and while stirring there are added 2.5 l of cocoa flavor and polyethylene glycol q.s. to a volume of 50 l, providing an oral drop solution comprising 10 mg/ml of the A.I. The resulting solution is filled into suitable containers.

EXAMPLE 16: Oral Solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and them, after 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE 17: Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE 18: Film-coated Tablets

Preparation of Tablet Core

A mixture of 100 g of the A.I., 570 g lactose and 200 g starch is mixed well and thereafter humidified with a solution of 5 g sodium dodecyl sulfate and 10 g polyvinylpyrrolidone (Kollidon-K 90®) in about 200 ml of water. The wet powder mixture is sieved, dried and sieved again. Then there are added 100 g microcrystalline cellulose (Avicel®) and 15 g hydrogenated vegetable oil (Sterotex ®). The whole is mixed well and compressed into tablets, giving 10.000 tablets, each comprising 10 mg of the active ingredient.

Coating

To a solution of 10 g methyl cellulose (Methocel 60 HG®) in 75 ml of denaturated ethanol there is added a solution of 5 g of ethyl cellulose (Ethocel 22 cps ®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-I-2109®) and the whole is homogenated. The tablet cores are coated with the thus obtained mixture in a coating apparatus.

EXAMPLE 19: Injectable Solutions 1.8 g methyl 4-hydroxybenzoate and 0.2 g propyl 4-hydroxybenzoate are dissolved in about 0.5 l of boiling water for injection. After cooling to about 50° C. there are added while stirring 4 g lactic acid, 0.05 g propylene glycol and 4 g of the A.I. The solution is cooled to room temperature and supplemented with water for injection q.s. ad 1 l volume, giving a solution of 4 mg A.I. per ml. The solution is sterilized by filtration (U.S.P. XVII p. 811) and filled in sterile containers.

EXAMPLE 20: Suppositories 3 g A.I. is dissolved in a solution of 3 g 2,3-dihydroxybutanedioic acid in 25 ml polyethylene glycol 400. 12 g surfactant (SPAN®) and triglycerides (Witepsol 555®) q.s. ad 300 g are molten together. The latter mixture is mixed well with the former solution. The thus obtained mixture is poured into moulds at a temperature of 37°–38° C. to form 100 suppositories each containing 30 mg of the A.I.

We claim:

1. A compound having the formula

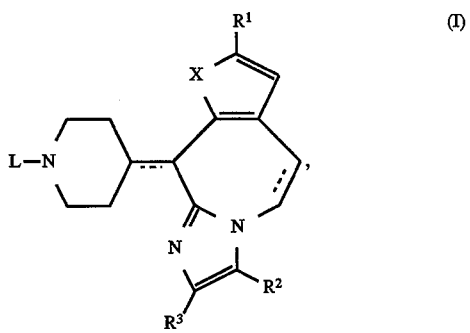

a pharmaceutically acceptable addition salt or a stereochemically isomeric form thereof, wherein
  each of the dotted lines independently represents an optional bond;
  $R^1$ represents hydrogen, $C_{1-4}$alkyl, halo, ethenyl substituted with hydroxycarbonyl or $C_{1-4}$alkyloxycarbonyl, hydroxy$C_{1-4}$alkyl, formyl, hydroxycarbonyl or hydroxycarbonyl$C_{1-4}$alkyl;
  $R^2$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl or hydroxycarbonyl;
  $R^3$ represents hydrogen, $C_{1-4}$alkyl, hydroxy$C_{1-4}$alkyl, phenyl or halo;
  X represents O, S or $NR_4$;
  $R^4$ represents hydrogen, $C_{1-6}$alkyl or $C_{1-4}$alkylcarbonyl;
  L represents hydrogen; $C_{1-6}$alkyl; $C_{1-6}$alkyl substituted with one substituent selected from the group consisting of hydroxy, $C_{1-4}$alkyloxy, hydroxycarbonyl, $C_{1-4}$alkyloxycarbonyl, $C_{1-4}$alkylaminocarbonyl, $C_{1-4}$alkyloxycarbonylamino, $C_{1-4}$alkyloxycarbonyl$C_{1-4}$alkyloxy, hydroxycarbonyl$C_{1-4}$alkyloxy, $C_{1-4}$alkylaminocarbonylamino, $C_{1-4}$alkylaminothiocarbonylamino, aryl and aryloxy; $C_{1-6}$alkyl substituted with both hydroxy and aryloxy; $C_{3-6}$alkenyl; $C_{3-6}$alkenyl substituted with aryl;
  wherein each aryl is phenyl or phenyl substituted with halo, cyano, hydroxy, $C_{1-4}$alkyl, $C_{1-4}$alkyloxy or aminocarbonyl or,
  L represents a radical of formula
    —Alk-y-$Het^1$(a-1),
    —Alk-NH-CO-$Het^2$(a-2) or
    —Alk-$Het^3$(a-3); wherein
  Alk represents $C_{1-4}$alkanediyl;
  Y represents O, S or NH;
  $Het^1$, $Het^2$ and $Het^3$ each represent furanyl, thienyl, oxazolyl, thiazolyl or imidazolyl each optionally substituted with one or two $C_{1-4}$alkyl substituents; pyrrolyl or pyrazolyl optionallly substituted with formyl, hydroxy$C_{1-4}$alkyl, hydroxycarbonyl, $C_{1-4}$alkyloxycarbonyl or with one or two $C_{1-4}$alkyl substituents; thiadiazolyl or oxadiazolyl optionally substituted with amino or $C_{1-4}$alkyl; pyridinyl, pyrimidinyl, pyrazinyl or pyridazinyl each optionally substituted with $C_{1-4}$alkyl, $C_{1-4}$alkyloxy, amino, hydroxy or halo; and
  $Het^3$ may also represent 4,5-dihydro-5-oxo-1H-tetrazolyl substituted with $C_{1-4}$alkyl, 2-oxo-3-oxazolidinyl, 2,3-dihydro-2-oxo-1H-benzimidazol-l-yl or a radical of formula

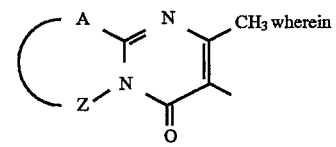

A-Z represents S-CH=CH, S-$CH_2$-$CH_2$, S-$CH_2$-$CH_2$-$CH_2$, CH=CH-CH=CH, or $CH_2$-$CH_2$-$CH_2$-$CH_2$.

2. A compound according to claim 1 wherein X represents S.

3. A compound according to claim 2 wherein $R^1$, $R^2$ and $R^3$ are hydrogen.

4. A compound according to claim 1 wherein said compound is 6,10-dihydro-10-(1-methyl-4-piperidinylidene)-5H-imidazo[1,2-a]thieno[2,3-d]azepine, the stereoisomers and the pharmaceutically acceptable addition salts thereof.

5. A pharmaceutical composition comprising as an active ingredient a therapeutically effective amount of a compound as defined in claim 1 and a pharmaceutically acceptable carrier.

6. A compound having the formula

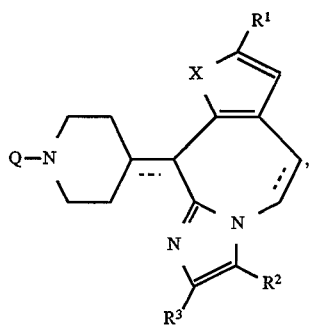

(VII)

an addition salt or a stereochemically isomeric form thereof, wherein each of the dotted lines, X, $R^1$, $R^2$ and $R^3$ are as defined in claim 1;

Q represents $C_{1-6}$alkyloxycarbonyl, $C_{1-4}$alkylcarbonyl or $C_{1-6}$alkyl substituted with halo, cyano, amino, or methylsulfonyloxy.

7. A compound having the formula

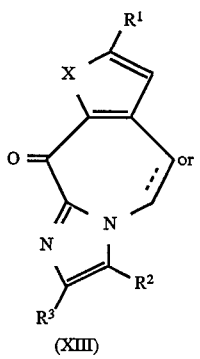

(XIII)

-continued

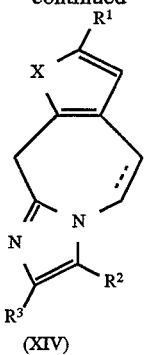

(XIV)

an addition salt or a stereochemically isomeric form thereof, wherein the dotted line, X, $R^1$, $R^2$ and $R^3$ are as defined in claim 1.

8. A method for the treatment of allergic disease which comprises administering to a warm blooded animal suffering from allergic disease a therapeutically effective amount of a compound as defined in claim 1.

9. A method for the treatment of allergic disease which comprises administering to a warm blooded animal suffering from allergic disease a therapeutically effective amount of a compound as defined in claim 2.

10. A method for the treatment of allergic disease which comprises administering to a warm blooded animal suffering from allergic disease a therapeutically effective amount of a compound as defined in claim 3.

11. A method for the treatment of allergic disease which comprises administering to a warm blooded animal suffering from allergic disease a therapeutically effective amount of a compound as defined in claim 4.

12. A pharmaceutical composition comprising as an active ingredient a therapeutically effective amount of a compound as defined in claim 2 and a pharmaceutically acceptable carrier.

13. A pharmaceutical composition comprising as an active ingredient a therapeutically effective amount of a compound as defined in claim 3 and a pharmaceutically acceptable carrier.

14. A pharmaceutical composition comprising as an active ingredient a therapeutically effective amount of a compound as defined in claim 4 and a pharmaceutically acceptable carrier.

* * * * *